(12) United States Patent
Kimmitt et al.

(10) Patent No.: US 8,050,487 B2
(45) Date of Patent: Nov. 1, 2011

(54) CABINET DOOR FINISH REPLICATION SYSTEM

(75) Inventors: Rick L. Kimmitt, Tipton, MI (US); John R. Kolin, Adrian, MI (US); William B. Birkett, Plymouth, MI (US)

(73) Assignee: Merillat Industries, LLC, Adrian, MI (US)

( * ) Notice: Subject to any disclaimer, the term of this patent is extended or adjusted under 35 U.S.C. 154(b) by 794 days.

(21) Appl. No.: 12/030,298

(22) Filed: Feb. 13, 2008

(65) Prior Publication Data

US 2009/0202132 A1 Aug. 13, 2009

(51) Int. Cl.
*G06K 9/00* (2006.01)

(52) U.S. Cl. .................................................. 382/141

(58) Field of Classification Search .................. None
See application file for complete search history.

(56) References Cited

U.S. PATENT DOCUMENTS

| | | | |
|---|---|---|---|
| 2006/0121231 A1* | 6/2006 | Lerner et al. | 428/40.1 |
| 2007/0091336 A1* | 4/2007 | Abad Peiro et al. | 358/1.9 |
| 2010/0128318 A1* | 5/2010 | Noffke et al. | 358/3.26 |

FOREIGN PATENT DOCUMENTS

AU 1991088901 A * 6/1992

* cited by examiner

*Primary Examiner* — Brian Werner

(74) *Attorney, Agent, or Firm* — Carlson, Gaskey & Olds

(57) ABSTRACT

Cabinet doors are compared to color samples as a quality control check on the colors of the manufacture doors. The color samples are obtained by selecting doors which have acceptable color, and capturing those images into a computer readable format. These captured images may then be printed, stored, transmitted, etc.

13 Claims, 2 Drawing Sheets

CABINET DOOR FINISH REPLICATION SYSTEM

BACKGROUND OF THE INVENTION

This application relates to a system for ensuring uniform color of finishes for cabinet doors.

Cabinets for modern residential applications are often sold in large retail locations. Typically, a sample cabinet may be provided at the retail location, and samples of all possible colors for the cabinets will also be provided. Consumers may order a cabinet, and the cabinets manufactured at a remote factory are shipped to the consumer.

Some quality control is required to ensure the color of the actual manufactured cabinet and its doors are close to the color presented to the consumer when making the purchase. Thus, it is known in the prior art to have sample doors maintained at a manufacturing facility that can be compared to the manufactured doors to ensure the manufactured doors are within an acceptable color range. It is typical that doors of a nominal, acceptable light extreme and an acceptable dark extreme are selected, and actual manufactured doors are compared to these two samples to ensure the manufactured doors are within the range. Typically, sample doors are selected from manufactured doors to provide the extreme samples, and must be replaced periodically.

The use of the actual selected doors does raise some concerns, however. First, over time, the range between the extreme light and extreme dark doors can vary. This is true because wood substrate variations and stain material variations exist from lot to lot. In addition, the doors may be manufactured at several facilities spaced across the country and even across continents. As such, it is difficult to maintain any set standard for the color of the manufactured doors that can be ensured to be within an acceptable range of the sample doors which have been utilized to make the consumer sale.

SUMMARY OF THE INVENTION

In the disclosed embodiment of this invention, standard samples for nominal, extreme light and extreme dark doors are selected and are scanned into a computer program. The scanned image is processed utilizing known processing techniques, and the image may then be printed and attached to an underlying door blank. This can then be utilized as the sample. This stored image will not change over time, but will instead be a fixed reference level. In addition, the same stored image can be sent to various manufacturing locations such that more uniform standards and limits are ensured across several manufacturing locations.

These and other features of the present invention can be best understood from the following specification and drawings, the following of which is a brief description.

DETAILED DESCRIPTION OF A PREFERRED EMBODIMENT

Figure 1:
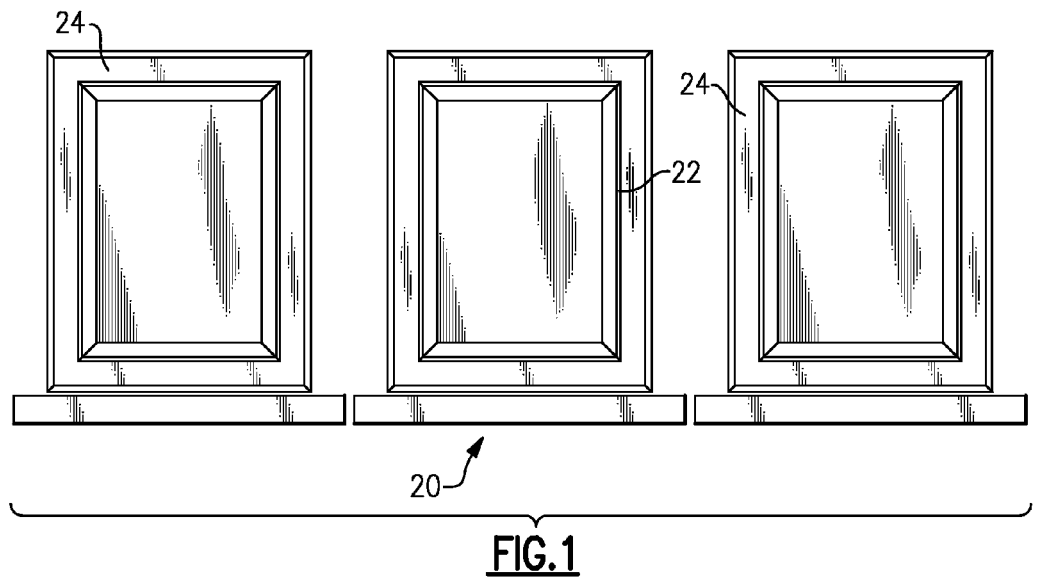
FIG. 1 shows two cabinet doors being compared.

As shown in FIG. 1, a location 20 is utilized for comparing a manufactured door 22 to a sample door 24. The sample door of the present invention is manufactured by printing a scanned stored image, and adhering that image to a door blank. Programs are known that print an image on a material that may have an adhesive backing to be secured to the blank, as an example. If the manufactured door 22 is lighter than a dark extreme sample 24, and darker than the light extreme sample 24, the manufactured door 22 is seen as acceptable.

Figures 2, 3:
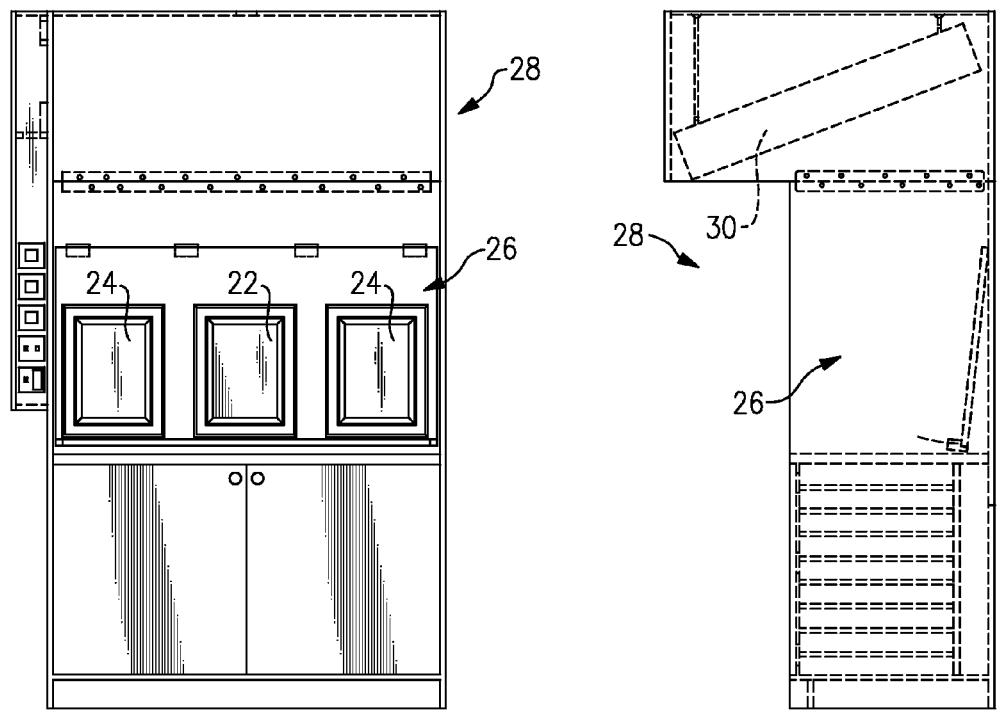
FIG. 2 shows a light booth which is typically utilized for this comparison.
FIG. 3 is a side view of the FIG. 2 light booth.

FIG. 2 shows a light booth 28 which is utilized for the inspection discussed above. The doors 22 and 24 are placed on easels 26 within the light booth 28. As can be appreciated from FIG. 3, the easels 26 may pivot about an upper point. A bank of lights 30 is positioned above the doors. Inspectors inspect the manufactured doors 22 to ensure they can conform to the standard set by the samples 24.

Figure 4:
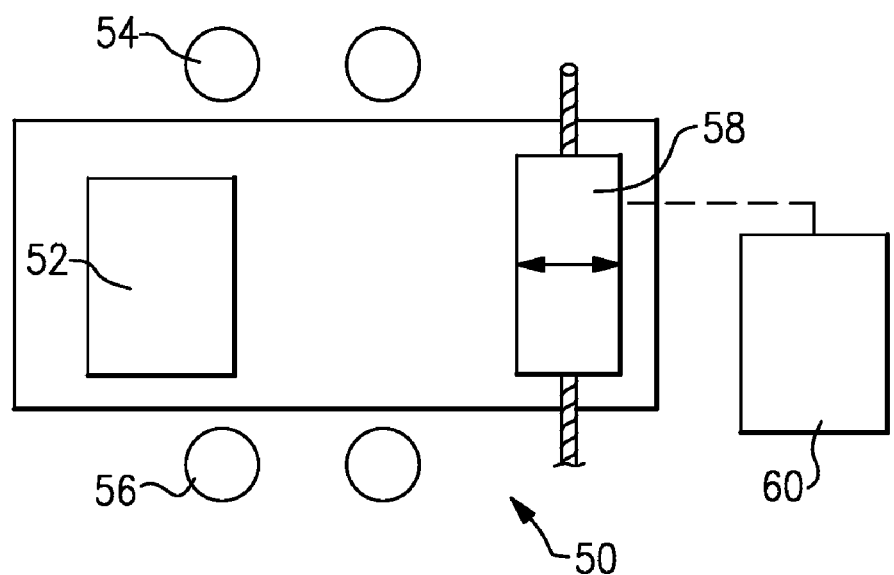
FIG. 4 is a schematic view of a first step in the present invention.
Figure 5:
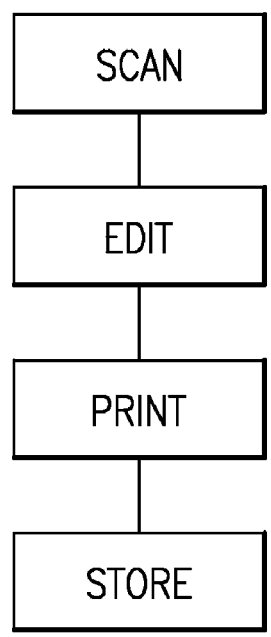
FIG. 5 is a flowchart of the present invention.

The present invention begins with a method shown schematically in FIG. 4. A scanner 50 is utilized to scan an image of a door 52 which will set the sample. Light banks 54 and 56 are positioned on each side of a scanning bed. A scanning bed moves under camera 58 relative to the door 52 and captures its image. The scanner may be a Cruse scanner, which is known in the industry, and utilized such as to scan large artwork. Applicant has discovered that turning off one of the banks 54 or 56 is desirable to gain a more accurate image of how the door will appear in the viewing booth.

The captured image from the camera 58 is delivered to a computer 60. Within the computer 60, or in another computer, the image may be processed utilized photoshop techniques, and to enhance the image as desired.

Eventually, the image is printed and put onto a door blank. That door blank with the printed image is then utilized as the standards.

A nominal, light extreme and a dark extreme will be prepared for use in the inspection booth. The image is also stored for future use. Also, the image may be transmitted to other remote locations such that a single standard may be provided across the entire range of factories which may be manufacturing doors of a similar desired color.

In one example method of this invention, real wood doors are utilized. The doors were scanned to obtain high-resolution images, with the Cruse scanner. The Cruse scanner was originally developed for reproduction of museum artwork, and has a large bed (about 4×6') that moves side-to-side by a precision lead screw drive. A line-scan camera was utilized and was mounted above the bed, pointed downward toward the item to be scanned, here the door standard. The bed moved underneath the camera, and the item was scanned line-by-line as it traveled.

To obtain a scan that resembles the actual wood in the inspection booth, as mentioned above, a bank of lights on one side of the scanning region was turned off, so that light came from one side only. This produced an appearance nearly identical to what is seen in an inspection booth.

The scans were made at a resolution of 360 dpi, and have a 16-bit depth. A custom ICC profile of the scanner was made, which is assigned to the images. Image files were saved in RGB TIFF format. The raw scans would produce prints that are perfectly acceptable for most applications. However, applicant has discovered additional benefit from fine-tuning color adjustments of these raw scans. Adobe Photoshop is utilized for this fine-tuning.

The raw scans are opened in Photoshop and converted to a new color space, which is one created for rendering wood colors. A working space was defined mathematically by specifying three additive primaries, and the tonality of those primaries. A gamut of colors among the different types of wood is relatively small, and thus Applicant was able to gain resolution for color adjustments by building a working space with a much smaller than normal gamut, when compared to many other applications.

Once the scans were converted to the working space, they were saved in Photoshop's layered file format (PSD). This format allows complex color editing through the use of adjustment layers. Adjustment layers define changes to the underlying layers, but do not actually alter those layers. The changes are applied by a "flattening" step, which creates a "rendition" file, actually used to make prints. This preserves the integrity of the original scanned image, so that it may be edited repeatedly without degradation. That is the "fine tuning" is performed without losing the original scanned image, such that one can return to this original image.

The flattened files were saved in Lab TIFF format. Lab is a standard color space defined by the CIE. By saving files in this format, Applicant ensured that they be printable in the future, on entirely new printing devices. These files were the master images which were stored to print future replications.

The editing of the images started by making an overall color adjustment. Then, Applicant looked at the various elements of the wood, such as background, tick and grain, etc. These elements may require secondary adjustments. Those adjustments are made on individual layers, using marks to isolate any details that one wishes to alter. Small adjustments have an effect on the perceived overall color balance, and may require further trimming of the overall color balance.

Once the images were printed and attached to wood blanks, the results were checked in an inspection booth such as will be utilized in manufacturing plants. The appearance of the wood has been found to be very dependent on viewing geometry, and the spectral composition of the lighting, and in particular the combination of daylight and incandescent lighting that may exist in the environment. D65 light bulbs may be used to replicate daylight. The printed images made by the method of this application appear more stable under varying conditions than the actual manufacturing doors, and some further effort in resolving these differences may be made in the future.

Once the edited image file has been fine-tuned to a sufficient degree, a full print was made and mounted onto a particle board blank, and known as engineered wood. A pressure sensitive adhesive filled with gray pigment may be utilized to minimize any color change caused by mounting the print. The edges of the wood were then painted black. A clear plastic channel was then placed on the long edges of this sample to prevent damage from handling.

In the example embodiment, the printer was an Epson 4800, Epson Ultra chrome K3 inks were used; the media was proofing paper white semi-matte S042003; the adhesive was seal print mount ultra. Of course, many other type scanners, printers, inks, media, adhesive, and all other particular items utilized for this example may be replaced by other materials, components, etc. The above is merely meant as one example method performed according to this invention.

Although embodiments of this invention have been disclosed, a worker of ordinary skill in this art would recognize that certain modifications would come within the scope of this invention. For that reason, the following claims should be studied to determine the true scope and content of this invention.

What is claimed is:

1. A method of quality control for cabinet doors comprising the steps of:
   (a) capturing an image of at least two initial door standards in a computer while the door standards are illuminated, substantially more from one side than another, to correspond to an appearance of the door standards in an inspection booth;
   (b) storing the captured images;
   (c) printing the captured images and utilizing the printed captured images as uniform light extreme and dark extreme standards to compare to manufactured doors to ensure the color of the manufactured doors is acceptable when compared to the uniform standards; and
   (d) attaching the captured images to a door blank.

2. The method as set forth in claim 1, wherein a scanner bed moves relative to the initial door standards to capture the images.

3. The method as set forth in claim 2, wherein lights are provided during this movement on only one side of a path of travel.

4. The method as set forth in claim 1, wherein the captured images are edited and processed after capture, and before being printed and stored.

5. The method as set forth in claim 4, wherein layering techniques are used as part of the editing.

6. The method as set forth in claim 1, wherein said stored captured images are transmitted electronically to remote locations, at which step (c) is repeated.

7. The method as set forth in claim 1, where at least three captured images are used, and at least three initial door samples are used, with said at least three captured images providing a nominal, light extreme and a dark extreme.

8. A method of quality control for cabinet doors comprising the steps of:
   (a) providing first and second door blanks, said first and second door blanks including a respective first and second image attached thereto, wherein said first image is a uniform light extreme standard, and said second image is a uniform dark extreme standard, each of said first and second images having been captured from a respective door standard illuminated, substantially more from one side than another, to correspond to an appearance of the door standard in an inspection booth;
   (b) comparing a manufactured door to said first and second images to ensure the color of the manufactured doors is acceptable when compared to the uniform standards; and
   (c) repeating said step (b) with a plurality of different manufactured doors.

9. The method as set forth in claim 8, wherein said manufactured door is positioned between said first and second door blanks in said step (b).

10. The method as set forth in claim 8, wherein said first and second door blanks are positioned in the inspection booth during said steps (b) and (c).

11. The method as set forth in claim 10, wherein said first and second images are positioned in said inspection booth during said steps (b) and (c).

12. The method as set forth in claim 8, wherein said manufactured doors are acceptable when said manufactured doors are lighter than said dark extreme sample and darker than said light extreme sample.

13. The method as set forth in claim 1, wherein said manufactured doors are acceptable when said manufactured doors are lighter than said dark extreme sample and darker than said light extreme sample.

* * * * *